US011229712B2

(12) United States Patent
Albert et al.

(10) Patent No.: US 11,229,712 B2
(45) Date of Patent: Jan. 25, 2022

(54) IN VIVO DETECTION OF A XENON-BINDING CAGE MOLECULE

(71) Applicant: Lakehead University, Thunder Bay (CA)

(72) Inventors: Mitchell Albert, Thunder Bay (CA); Francis Hane, Thunder Bay (CA)

(73) Assignee: Lakehead University, Thunder Bay (CA)

( * ) Notice: Subject to any disclaimer, the term of this patent is extended or adjusted under 35 U.S.C. 154(b) by 305 days.

(21) Appl. No.: 15/607,842

(22) Filed: May 30, 2017

(65) Prior Publication Data

US 2017/0348439 A1 Dec. 7, 2017

Related U.S. Application Data

(60) Provisional application No. 62/345,098, filed on Jun. 3, 2016.

(51) Int. Cl.
| | | |
|---|---|---|
| *A61K 49/18* | (2006.01) | |
| *A61B 5/055* | (2006.01) | |
| *A61K 49/06* | (2006.01) | |
| *C01B 23/00* | (2006.01) | |

(52) U.S. Cl.
CPC ........... *A61K 49/189* (2013.01); *A61B 5/055* (2013.01); *A61K 49/06* (2013.01); *C01B 23/00* (2013.01)

(58) Field of Classification Search
CPC .................................................. A61K 49/189
See application file for complete search history.

(56) References Cited

U.S. PATENT DOCUMENTS

| 5,485,835 A | * | 1/1996 | Streek | A61M 15/02 128/203.12 |
| 7,867,477 B2 | * | 1/2011 | Driehuys | A61B 5/055 424/1.11 |
| 2002/0037253 A1 | * | 3/2002 | Pines | A61K 49/1815 424/9.321 |

(Continued)

OTHER PUBLICATIONS

Yanfei Wang and Ivan J. Dmochowski; Cucurbit[6]uril is an ultrasensitive 129Xe NMR contrast agent; Chem Commun (Camb). May 28, 2015; 51(43): 8982-8985. doi:10.1039/c5cc01826a. (Year: 2015).*

(Continued)

*Primary Examiner* — Joanne M Hoffman

(74) *Attorney, Agent, or Firm* — Michael R Williams; Ryan W Dupuis; Ade & Company Inc.

(57) ABSTRACT

Xenon based biosensors have the potential to detect and localize biomarkers associated with a wide variety of diseases. The development and nuclear magnetic resonance (NMR) characterization of cage molecules which encapsulate hyperpolarized xenon is imperative for the development of these xenon biosensors. We acquired $^{129}$Xe NMR spectra, and magnetic resonance images and a HyperCEST saturation map of cucurbituril (CB6) in whole bovine blood. We observed a mean HyperCEST depletion of 84% (n=5) at a concentration of 5 mM and 74% at 2.5 mM. Additionally, we collected these data using a pulsed HyperCEST saturation pre-pulse train with a SAR of 0.025 W/kg which will minimize any potential RF heating in animal or human tissue.

14 Claims, 7 Drawing Sheets

(56) References Cited

U.S. PATENT DOCUMENTS

| | | | | |
|---|---|---|---|---|
| 2002/0094317 | A1* | 7/2002 | Pines | A61K 49/1815 424/9.3 |
| 2005/0238726 | A1* | 10/2005 | Franks | A61K 33/00 424/600 |
| 2009/0297453 | A1* | 12/2009 | Driehuys | A61B 5/055 424/9.2 |
| 2011/0104075 | A1* | 5/2011 | Dmochowski | A61K 49/085 424/9.34 |
| 2014/0004043 | A1* | 1/2014 | Holman | A61K 49/189 424/1.81 |
| 2014/0288411 | A1* | 9/2014 | Shapiro | A61K 49/1809 600/420 |
| 2016/0030472 | A1* | 2/2016 | Billoet | A61K 31/4535 424/600 |
| 2017/0128910 | A1* | 5/2017 | Cooper | B01J 20/22 |
| 2019/0101545 | A1* | 4/2019 | DeBoef | C08L 101/00 |

OTHER PUBLICATIONS

Byoung Soo Kim, Young Ho Ko, Youngkook Kim, Hyeong Ju Lee, N. Selvapalam, Hee Cheon Lee and Kimoon Kim; Water soluble cucurbit[6]uril derivative as a potential Xe carrier for 129Xe NMR-based biosensors; Chem Comm; Accepted Apr. 21, 2008 First published as an Advance Article on the web May 19, 2008 (Year: 2008).*

John Nouls, Manuel Fanarjian, Laurence Hedlund, and Bastiaan Driehuys; A Constant-Volume Ventilator and Gas Recapture System for Hyperpolarized Gas MRI of Mouse and Rat Lungs; Concepts Magn Reson Part B Magn Reson Eng. Apr. 2011 ; 39B(2): 78-88. doi:10.1002/cmr.b.20192. (Year: 2011).*

Hane, Smylie, Li, Ruberto, Dowhos, Ball, Tomanek, DeBoef and Albert, "HyperCEST detection of cucurbit[6]uril in whole blood using an ultrashort saturation Pre-pulse train" Contrast Media Molecular Imaging, 11, pp. 285-290 (Year: 2016).*

Ilburn, "Perspectives of hyperpolarized noble gas MRI beyond 3He", Journal of Magnetic Resonance, 229, 2013, pp. 173-186 (Year: 2013).*

Jorg Dopfert, "Fast and Sensitive NMR Encoding for Reversibly Bound Xenon", Dissertation (Year: 2015).*

Wang, "Cucurbit[6]uril is an ultrasensitive 129Xe NMR contrast agent", Chem. Commun., 2015, 51, 8982-8985 (Year: 2015).*

Kim, "Cucurbit[6]uril-based polymer nanocapsules as a non-covalent and modular bioimaging platform for multimodal in vivo imaging", I Mater. Horiz., 2017, 4, 450-455 (Year: 2017).*

Schroder L et al: "Molecular imaging using a targeted magnetic resonance hyperpolarized biosensor", Science American Association for the Advancement of Science, vol. 314, Oct. 20, 2006, pp. 446-449, XP002476683, ISSN: 0036-8075, DOI: 10.1126/Science. 1131847.

Dowhos K et al: "Enhanced 129Xe Hyper-Cest Efficiency Using PK11195 Functionalized Cryptophane-A", International Society for Magnetic Resonance in Medicine, ISMRM, 2030 Addison Street, 7th Floor, Berkeley, CA 94704 USA, No. 3537, Apr. 28, 2014, XP040664565.

Khan N et al: "Cryptophane-Folate Biosensor for 129 Xe NMR", Bioconjugate Chemistry, vol. 26, No. 1, Jan. 21, 2015, pp. 101-109, XP55410380, ISSN: 1043-1802, DOI: 10.1021/bc5005526.

Wei Q et al: "Designing 129 Xe NMR Biosensors for Matrix Metalloproteinase Detection", Journal of the American Chemical Society, vol. 128, No. 40, Oct. 1, 2006, p. 13274-13283, XP55410483, US ISSN: 0002-7863, DOI: 10.1021/ja0640501.

Riggle B et al: "A "Smart" 129 Xe NMR Biosensor for pH-Dependent Cell Labeling", Journal of the American Chemical Society, vol. 137, No. 16, Apr. 29, 2015, pp. 5542-5548, XP55410400, US ISSN: 0002-7863, DOI: 10.1021/acs.5b01938.

Hane F et al: "In Vivo Hypercest Detection of Cucurbit(6)uril in Rat Abdomen", International Society for Magnetic Resonance in Medicine, ISMRM, 2030 Addison Street, 7th Floor, Berkeley, CA 94704 USA. No. 814, Apr. 22, 2016, XP040681857.

Hane F et al: "In Vivo detection of cucurbit(6)uril, a hyperpolarized xenon contrast agent for a xenon magnetic resonance imaging biosensor", Scientific Reports, vol. 7, Jan. 20, 2017, p. 41027, XP055410052, DOI: 10.1038/srep41027.

Hane F: "HyperCEST MRI Detection of the Cucurbit(6)uril Xenon Cage in the Rat in vivo", Mol Imaging Biol, vol. 18 (Suppl. 2), Nov. 21, 2016, XP055410169.

* cited by examiner

IN VIVO DETECTION OF A XENON-BINDING CAGE MOLECULE

PRIOR APPLICATION INFORMATION

The instant application claims the benefit of US Provisional Patent Application U.S. Ser. No. 62/345,098, filed Jun. 3, 2016 and entitled "IN VIVO DETECTION OF A XENON-BINDING CAGE MOLECULE", the contents of which are incorporated herein by reference.

BACKGROUND OF THE INVENTION

Hyperpolarized (HP) gas based magnetic resonance imaging (MRI) biosensors have the potential to detect very small concentrations of molecular targets in the body (1). Such biosensors should be able to image a wide range of pathologies from cancer to inflammation, based on at least one distinct biomarker (2). The extreme sensitivity of these biosensors is a combination of the hyperpolarization of noble gases, such as $^{129}$Xe (3, 4) and the ability of cage molecules to rapidly exchange polarized gas atoms which can be "saturated", allowing their detection by applying the Hyperpolarized Chemical Exchange Saturation Transfer (HyperCEST) method (5, 6). The combination of these two techniques results in a signal-noise ratio increase of up to $10^9$ over thermally polarized $^{129}$Xe noble gas (7).

A number of groups have demonstrated the synthesis of imaging biosensors and have tested them in vitro (1, 8-10). These biosensors comprise a 129Xe encapsulating cage molecule conjugated to an affinity tag that can bind to a small molecule of interest such as an ion or protein (2). The cage molecules and nanostructures suitable for HyperCEST which have been studied by $^{129}$Xe NMR include cryptophanes (1, 11-13), cucurbiturils (14, 15), gas vesicles (8), perfluorooctyl bromide (16), and bacterial spores (17). Cryptophanes have been conjugated to affinity tags to bind targets such as zinc (9), toxic metal ions (10), CD14 cells (7), the cancer-associated HER2 receptor (8), and the inflammation-marking peripheral benzodiazapene receptor (PBR) (18) amongst others (19-21). Translating in vitro experiments to in vivo imaging requires overcoming a number of challenges including potential toxicity, solubility and the rapid depolarization of $^{129}$Xe in blood (22-25). Despite the challenges associated with enhanced relaxation in blood, a number of groups have successfully reported other systems such as cell cultures (1, 8, 26-29) and blood plasma (14, 30). These experiments were completed on high-field, small bore, high-resolution MR spectrometers. Our experiments were completed using a clinical whole body 3T MR scanner, which bodes well for the clinical translation of this technique.

Hyperpolarized (HP) xenon magnetic resonance imaging (MRI) (4) biosensors have the potential to provide high sensitivity and high resolution imaging of pathologies within the body (8, 35). The basis of these imaging biosensors is a cage molecule, acting as an MRI contrast agent, which is a supramolecular host that can reversibly encapsulate a guest HP xenon atom. These properties provide a unique and detectable magnetic resonance (MR) chemical frequency shift for the xenon atom inside the cage (5, 36). Combined with hyperpolarization, which creates a nuclear spin polarization of xenon far beyond thermal equilibrium conditions, these biosensors have the potential to provide a signal enhancement of up to a billion times above conventional xenon MR (5), thus providing high resolution MR images with Positron Emission Tomography (PET)-like sensitivity, yet with the spatial resolution of MRI. Despite this promise, xenon biosensors have yet to be detected within a living animal model following their intravenous administration.

SUMMARY OF THE INVENTION

According to an aspect of the invention, there is provided an in vivo method of magnetic resonance imaging comprising:
  injecting a solution comprising tagged supramolecular xenon cages, into an individual;
  while ventilating said individual with a mixture of oxygen gas and hyperpolarized xenon gas such that xenon in the tagged supramolecular xenon cages exchange with the hyperpolarized xenon gas, thereby forming tagged supramolecular hyperpolarized xenon cages, said supramolecular tag hyperpolarized xenon cages having a chemical shift frequency,
  applying a pulse at the chemical shift frequency, thereby depolarizing xenon in the tagged supramolecular hyperpolarized xenon cages;
  generating an on-resonance xenon magnetic resonance image of the individual at the chemical shift frequency;
  applying a pulse at an off-resonance frequency;
  generating an off-resonance xenon magnetic resonance image of the individual at the off-resonance frequency; and
  subtracting the off-resonance image from the on-resonance image, thereby imaging the location of the tagged supramolecular xenon cages within the individual.

As discussed herein, the imaging may be of a region of interest of the individual, for example, a specific organ or tissue portion. In some embodiments the individual is a human.

The tagged supramolecular cages may be selected from the group consisting of tagged cucurbituril cages, tagged cryptophane cages, tagged calixararene cages, tagged pillarene cages, tagged rotaxane cages and tagged pseudorotaxane cages.

In some embodiments, the tagged supramolecular cages are tagged cucurbituril cages.

According to a further aspect of the invention, there is provided an in vivo method of magnetic resonance imaging comprising:
  injecting a solution comprising tagged cucurbituril xenon cages into an individual;
  while ventilating said individual with a mixture of oxygen gas and hyperpolarized xenon gas such that xenon in the tagged cucurbituril xenon cages exchanges with the hyperpolarized xenon gas, thereby forming tagged cucurbituril hyperpolarized xenon cages, said tagged cucurbituril hyperpolarized xenon cages having a chemical shift frequency;
  applying a pre-pulse at the chemical shift frequency, thereby depolarizing xenon in the tagged cucurbituril hyperpolarized xenon cages;
  generating an on-resonance xenon magnetic resonance image of the individual at the chemical shift frequency;
  applying a pulse at an off-resonance frequency;
  generating and an off-resonance xenon magnetic resonance image of the individual; at the off-resonance frequency; and
  subtracting the off-resonance image from the on-resonance image, thereby imaging the location of the tagged cucurbituril xenon cages within the individual.

DESCRIPTION OF THE PREFERRED EMBODIMENTS

Figure 1:
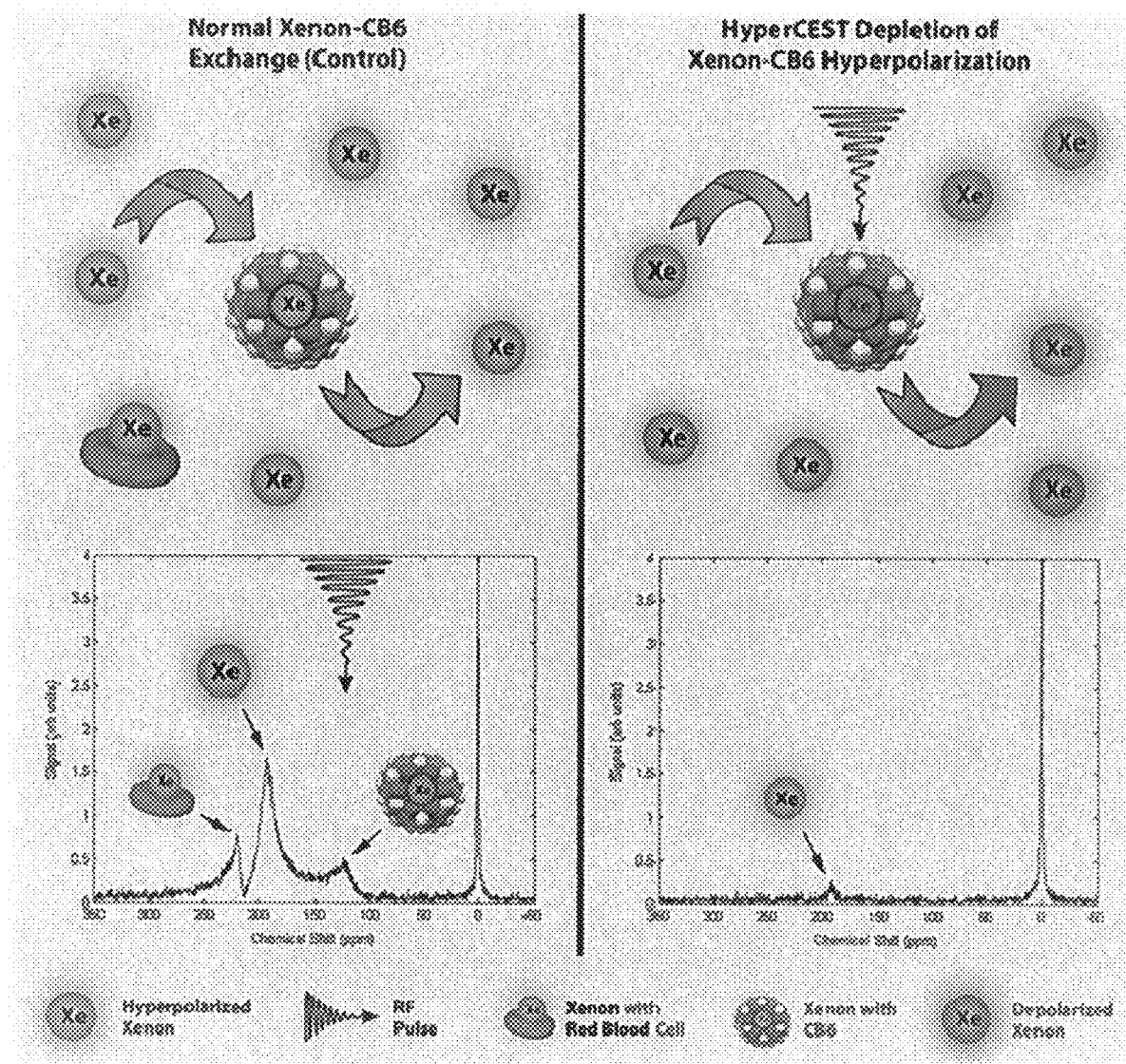
FIG. 1—(Left) The population of Xe nuclei represented in red are hyperpolarized, which infers that there are more nuclei in the spin down state than spin up. The population of Xe nuclei represented in blue are depolarized (or saturated) and have an approximately equal number of up and down spins. $^{129}$Xe NMR spectrum of Xe exchanging in cucurbituril The xenon dissolved in the plasma is represented by a peak at +191.4 ppm. The hyperpolarized $^{129}$Xe continually exchanges in and out of the CB6 resulting in a Xe-CB6 peak at 124.3 ppm. The xenon-red blood cell complex is represented by a peak at +219.4 ppm. (Right) a HyperCEST pulse is applied at the Xe-CB6 peak of +124.3 ppm (−68 ppm from dissolved xenon peak) corresponding to the chemical shift of the CB6 peak. The xenon encapsulated by the CB6 becomes depolarized and exchanges with the solvent pool of hyperpolarized xenon. Fewer hyperpolarized xenon atoms are now in the solvent pool resulting in a large reduction in the dissolved Xe peak at +191.4 ppm.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Herein, we demonstrate the first example of the in vivo detection of a HP gas MRI contrast agent using HyperCEST-enhanced $^{129}$Xe MRI, of the cucurbituril (CB6) cage molecule, within the vasculature of a live rat. By having the rat breathe xenon gas, which dissolves in the blood and interacts with the injected CB6 cages circulating in the vasculature, we were able to successfully detect the presence of CB6 in the brain, heart, aorta, carotid arteries, kidneys, and eventually followed its renal clearance into the bladder. These results translate this technique from in vitro studies to pre-clinical studies and thence to clinical use. Our work demonstrates the feasibility of employing HP gas MRI biosensors as a possible replacement to PET imaging because of its superior resolution, facile synthesis, lower cost, and its absence of ionizing radiation. Our results will form the basis for the development of targeted imaging biosensors that can detect specific areas of pathologies within the body using HP xenon MRI. These results translate to earlier detection of specific pathologies, and provide treatment monitoring in longitudinal studies.

The Hyperpolarized Xenon Chemical Exchange Saturation Transfer (HyperCEST) MRI technique multiplies the signal enhancement of the hyperpolarization of $^{129}$Xe (37) with the chemical exchange signal enhancement produced by the CEST MRI pulse sequence (5). This method takes advantage of the continual diffusion of HP xenon atoms in and out of the cage molecule, which provides a unique chemical shift from the frequency of HP xenon atoms dissolved in solution. A HyperCEST saturation pre-pulse is applied at the chemical shift frequency of xenon within the cage molecule, thereby depolarizing the xenon atoms. As the depolarized xenon atoms exchange out of the cage molecule, they are replaced by polarized atoms from the reservoir of dissolved $^{129}$Xe atoms in solution. This results in a decrease of polarized nuclei in the dissolved-phase xenon reservoir, thereby reducing its signal. Subtracting the on-resonance HyperCEST signal from the off-resonance control signal, results in a signal enhancement of up to 4 orders of magnitude above the signal enhancement afforded by the hyperpolarization process (5). Similarly, in imaging, by subtracting the "control" off-resonance xenon image from the saturated, pulsed on-resonance image, a HyperCEST saturation map can be created, showing the location of the cage molecules. By conjugating the cage molecule with an affinity tag, a HP xenon MR imaging biosensor can be created that can spatially localize areas of pathology (7, 8, 26, 35).

In this work we acquired $^{129}$Xe NMR spectra, HyperCEST depletion, MR images, and HyperCEST image saturation maps of a CB6 cage molecule within the vasculature of a living rat. We demonstrate a novel pulsed saturation pre-pulse sequence that can overcome some of the potential challenges associated with HP $^{129}$Xe biosensors. These developments demonstrate that a wide variety of proposed cage molecules and Imaging biosensors can be used in animals.

According to an aspect of the invention, there is provided an in vivo method of magnetic resonance imaging comprising:

injecting a solution comprising tagged supramolecular cages into an individual;

while ventilating said individual with a mixture of oxygen gas and hyperpolarized xenon gas such that xenon in the tagged supramolecular xenon cages exchanges with the hyperpolarized xenon gas, thereby forming tagged supramolecular hyperpolarized xenon cages, said tagged supramolecular hyperpolarized xenon cages having a chemical shift frequency;

applying a pulse at the chemical shift frequency, thereby depolarizing xenon in the tagged supramolecular hyperpolarized xenon cages;

generating an on-resonance xenon magnetic resonance image of the individual at the chemical shift frequency;

applying a pulse at an off-resonance frequency;

generating an off-resonance xenon magnetic resonance image of the individual at the off-resonance frequency; and subtracting the off-resonance image from the on-resonance image, thereby imaging the location of the tagged supramolecular cages within the individual.

The tagged supramolecular cages may be selected from the group consisting of tagged cucurbituril cages, tagged cryptophane cages, tagged calixararene cages, tagged pillarene cages, tagged rotaxane cages and tagged pseudorotaxane cages.

In some embodiments, the tagged supramolecular cages are tagged cucurbituril xenon cages.

As discussed herein, the imaging may be of a region of interest of the individual, for example, a specific organ or tissue portion. In some embodiments the individual is a human.

According to a further aspect of the invention, there is provided an in vivo method of magnetic resonance imaging comprising:

injecting a solution comprising tagged cucurbituril xenon cages into an individual;

while ventilating said individual with a mixture of oxygen gas and hyperpolarized xenon gas such that xenon in the tagged cucurbituril xenon cages exchanges with the hyperpolarized xenon gas, thereby forming tagged cucurbituril hyperpolarized xenon cages, said tagged cucurbituril hyperpolarized xenon cages having a chemical shift frequency;

applying a pre-pulse at the chemical shift frequency, thereby depolarizing xenon in the tagged cucurbituril hyperpolarized xenon cages;

generating an on-resonance xenon magnetic resonance image of the individual at the chemical shift frequency;

applying a pulse at an off-resonance frequency;

generating and an off-resonance xenon magnetic resonance image of the individual; at the off-resonance frequency; and subtracting the off-resonance image from the on-resonance image, thereby imaging the location of the tagged cucurbituril xenon cages within the individual.

As will be appreciated by one of skill in the art, the individual may be a human subject. Furthermore, the imaging may be of the entire body of the individual or may be of a specific region of the body, for example, a specific region of tissue or tissue type or a specific organ or limb or vascular area or the like.

The cucurbituril may be any suitable cucurbituril known in the art (14, 15). For example, the cucurbituril may be for example but by no means limited to cucurbituril, cucurbituriel, cucurbituril, cucurbituril, or cucurbituril In some embodiments, the cucurbituril is cucurbituril or CB6.

Alternatively, other tagged supramolecular xenon cages, such as for example but by no means limited to cryptophanes, calixerenes, liposomes, cyclodextrins, gas vesicles, perfluoro-octo bromide, bacterial spores, and viruses may be used within the invention. Specifically, as will be appreciated by one of skill in the art, any of these cage types which are non-toxic to the individual being imaged can be used within the invention.

As used herein, a "tag" refers to any molecule that can bind to a small molecule of interest such as an ion, protein or the like. For example, the "tag" may be an affinity tag, an antibody, a ligand or other similar suitable compound for interacting with or binding to a specific target.

As will be known by those of skill in the art, a number of previous HyperCEST contrast agents tested, including cryptophanes, were found to have toxic effects when tested in vivo. As will be appreciated by those of skill in the art, it is very difficult to predict in advance what molecules will be non-toxic due to the complexities of interactions in vivo.

Furthermore, CB6 could also have been ineffective in vivo. For example, CB6 could have failed to dissolve in solution or precipitate out in the blood or dissociate in the blood, thereby rendering CB6 useless for imagining in vivo.

Yet further, it is possible that the RF field strength might not have been strong enough to depolarize the xenon molecules in the cage or that not enough signal was generated from the xenon in the body due to depolarization from the interaction with the oxygen gas.

In some embodiments, it is a mixture of no more than about 80% xenon and at least about 20% oxygen. As will be apparent to those of skill in the art, use of less than 20% oxygen could potentially asphyxiate the subject.

In other embodiments, the mixture may be about 70 to about 80% xenon and about 20 to about 30% oxygen.

As will be apparent to one of skill in the art, a wide variety of pulse conditions, specifically, HyperCEST pulse conditions, may be used within the scope of the invention. For example, the pulse may be a pulse train or continuous or a wave or a continuous wave or any other such suitable arrangement known in the art. In some embodiments of the invention, the pre-pulse is a pre-pulse train of sixteen 6 ms 3-lobe sinc pulses with 3 ms pulse intervals.

As will be appreciated by one of skill in the art, the specific chemical shift frequency of a specific tagged cucurbituril-xenon cage may depend on several factors, for example, the specific cucurbituril used as well as the tag used for the cage construct. However, the specific chemical shift frequency for a given cage construct can be readily determined using the methods described herein. Furthermore, a wide variety of off-resonance frequencies are suitable to be used within the invention, as will be readily apparent to one of skill in the art. For example, in some embodiments the on-resonance pulse may be applied at +215 ppm and the off-resonance pulse may be applied at +124.3 ppm.

As will be apparent to one of skill in the art, proportionally larger doses of cucurbituril would be required for imaging in humans. Such doses will of course depend on many factors, including but by no means limited to the age, weight, height and general condition of the individual. Furthermore, it is maintained that such optimization is routine experimentation and is within the scope of the invention. While not wishing to be bound to a particular theory or hypothesis, it is believed by the inventors that for example about 10 ml of cucurbituril per kilogram of body weight of the human patient and about 1 L of xenon would be suitable.

Combining the MR active cage molecules with an antibody or other affinity tag as a targeting agent, a HP xenon MR Imaging biosensor would be created to spatially localize areas of pathology within the body. Such biosensors provide the imaging based support for personalized medicine. Personalized medicine and precision radiology require specialized imaging modalities that provide imaging biomarkers (39). These imaging biomarkers allow for the stratification of patients according to their phenotypic characteristics, which is a requirement of personalized medicine.

For example, antibodies known to bind to specific cancer-related antigens could be used as the tag within the invention for early stage diagnosis of certain cancers. Alternatively, by way of Illustration, the "tag" could be serotonin, which will bind to areas of atherosclerosis, or thioflavin which binds to areas of Alzhelmer's disease within the brain or deoxyglucose for cancer detection. Of course, other suitable tags for use in in vivo imaging will be readily apparent to one of skill in the art.

At present, molecular Imaging in deep tissue has been mainly restricted to PET and SPECT; these modalities, however, have a number of significant drawbacks. In addition, both require large capital investments in the form of dedicated scanners and cyclotrons to produce radioisotopes. While polarization hardware is not inexpensive, it is less expensive than PET hardware (40). Most significantly, HP xenon MRI is capable of much higher spatial resolution than PET imaging, making the localization of small lesions a possibility. PET scanners rely on the spatial resolution of CT or MRI scanners for anatomical localization; HP xenon MRI has the capability for obviating that necessity. Furthermore, since no Ionizing radiation is used, HP gas MRI biosensor imaging studies can be conducted more frequently than ionization based molecular imaging techniques.

With the demonstration of a HP xenon biosensor MRI contrast agent in vivo, the development and successful in vivo demonstration of targeted HP gas MRI biosensors that can image localized disease within whole, living organisms is a sound prediction.

The invention will now be further illustrated by way of examples; however, the invention is not necessarily limited to the Examples.

In a 2.5 mM CB6 solution dissolved in blood and PBS, we observed a peak at +192.4 ppm with respect to the xenon gas phase peak which corresponds to the xenon dissolved in blood plasma (FIG. 1, left panel). Additionally, a peak corresponding to the CB6 encapsulating xenon was observed at +124.3 ppm (FIG. 1, left panel). A peak at +219.4 ppm was observed which corresponds to the $^{129}$Xe bound to the red blood cells (RBC) (FIG. 1). Following the application of a pulsed saturation pre-pulse train of sixteen 6 ms 3-lobe sinc pulses with 3 ms pulse intervals at +124.3 ppm, we acquired the $^{129}$Xe NMR spectrum shown in FIG. 1. Following a HyperCEST saturation pre-pulse, we observed a large depletion (84%) in the dissolved phase xenon signal indicating polarization exchange from the CB6 into and out of the CB6 cage molecules.

Figure 2:
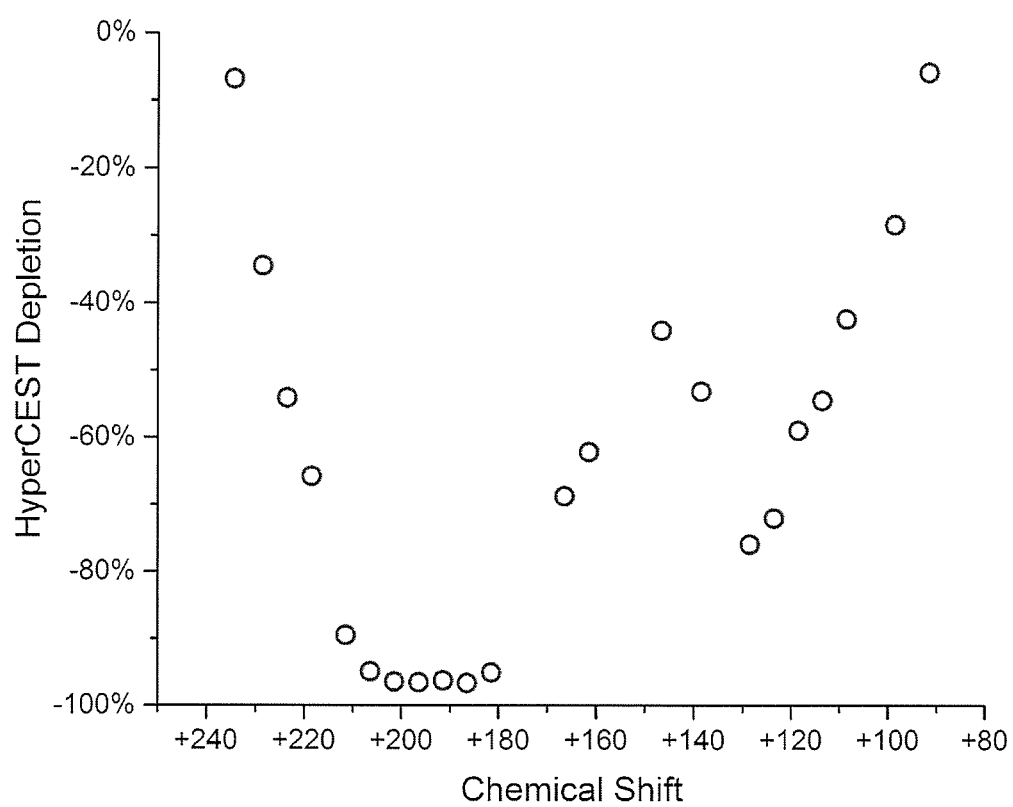
FIG. 2—HyperCEST depletion spectrum of CB6 in blood. A local minimum at +124.3 ppm indicates a 74% signal depletion when the solution is pulsed at +124.3 ppm, the chemical shift of the xenon-CB6 complex. Notice an almost complete HyperCEST depletion between +180 ppm and +207 ppm which corresponds to the xenon dissolved in plasma.

We continued to collect HyperCEST spectra by applying saturation pre-pulses at frequencies which were offset from the CB6 peak frequencies. Signal depletion for each saturation pre-pulse offset frequency is shown in the HyperCEST depletion spectrum shown in FIG. 2. Notice a high signal depletion corresponding to the CB6 and xenon-plasma peak at +191.4 ppm with lesser depletion as the saturation pre-pulse frequency is applied further away from these peaks. A local minimum is observed at +124.3 ppm, which corresponds to the chemical shift of the CB6/Xe complex.

We initially hypothesized that we would observe a HyperCEST depletion when saturation pre-pulses were applied at the RBC peak because of the exchange between the dissolved xenon pool and the xenon bound to the RBC. Somewhat counterintultively we did not observe this effect. Bifone, et al. calculated an Xe-RBC exchange rate of 50 s$^{-1}$ (22), which is considerably slower than the Xe-CB6 exchange of 1470 s$^{-1}$ (14). This slower exchange might be the reason why we did not observe a HyperCEST depletion when the RBC peak was saturated.

Figure 3:
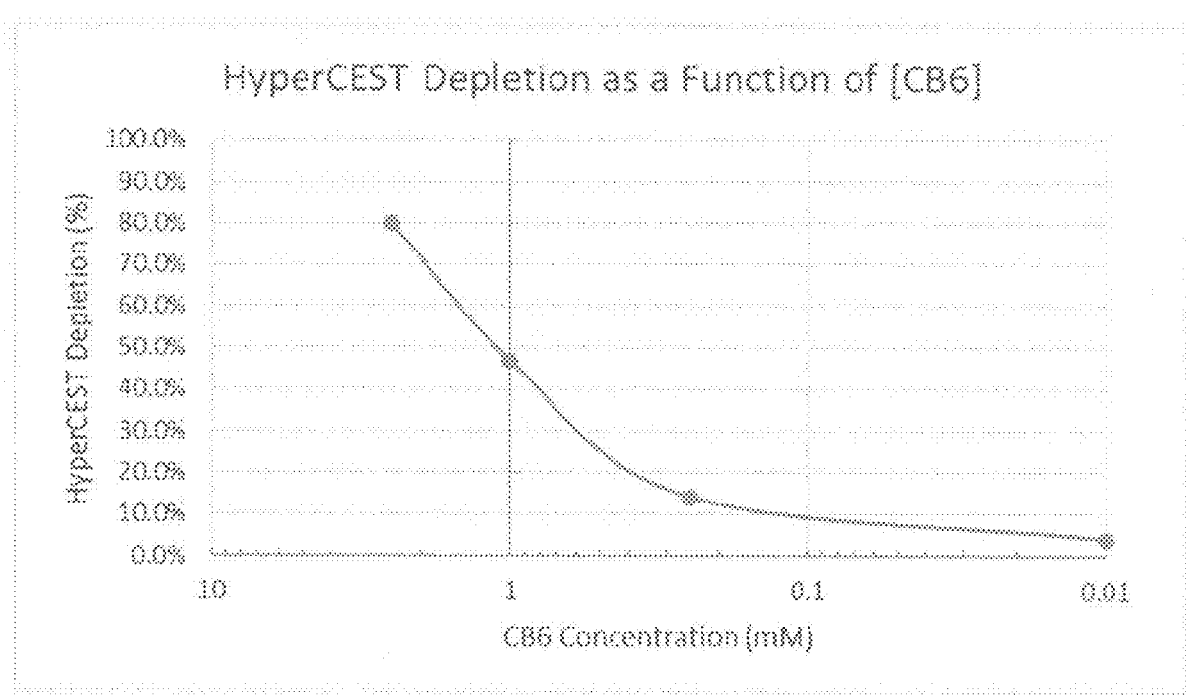
FIG. 3—HyperCEST depletion of CB6 as a function of CB6 concentration in whole bovine blood. A HyperCEST depletion of 80% was observed at 2.5 mM. This depletion was reduced to 14% at 250 µM. A HyperCEST depletion effect was observed down to a CB6 concentration of 10 µM.

We made serial dilutions of our CB6/blood and measured HyperCEST depletion as a function of concentration. We tested concentrations down to 10 μM of CB6 in blood. We measured a HyperCEST effect of 14% at a concentration of 250 μM (FIG. 3). A HyperCEST depletion was measurable down to 10 μM.

Figure 4:
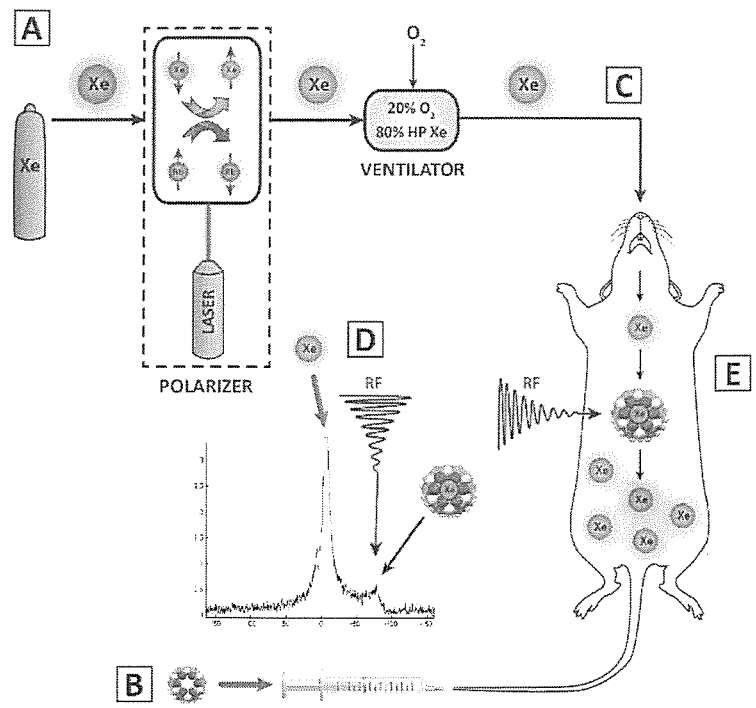
FIG. 4—(A) An off-resonant control 2D gradient echo image of 2.5 mM CB6 in blood. Within the FOV, the left circle is a 30 mL syringe containing CB6 in a blood solution. The right circle is a syringe containing only the blood solution but no CB6. Both syringes contain equal amounts of HP $^{129}$Xe. The two semi-circles in the bottom of the image are chemical shift artifacts from gas phase xenon present in the syringe. (B) The same set up as (A) but an image acquisition taken following on-resonance RF saturation pre-pulses at the Xe-CB6 chemical shift (124.3 ppm). (C) A HyperCEST saturation map of image B subtracted from image A and dividing each pixel by the off-resonance control image (A).

We obtained MR images of two syringes within the same field of view: one filled with a CB6 blood solution, the other with only a blood solution and no CB6 molecules (FIG. 4). Signal from the plasma, gas phase, and RBC-bound xenon is present in the control image (FIG. 4A). We observed a gas phase chemical shift artifact, offset by 43 pixels of 67.1 mm. Additionally, we observed a stronger gas phase signal from the control solution (right syringe) than the CB6 syringe (left syringe). We attribute this phenomenon to the differences in the extent of blood foam formation between the two solutions. The control solution foamed more than the CB6 solution, which provided a reservoir of gaseous hyperpolarized xenon to exchange with the xenon dissolved in the plasma providing a stronger xenon-plasma signal. Once a saturation pre-pulse train was applied (FIG. 4B), there was an almost complete depletion of dissolved phase xenon signal. A saturation map was produced (FIG. 4C) by normalizing each image by Its own background noise and subtracting the off-resonance control image from the Hyper- CEST saturation image and normalizing pixel-by-pixel, the off-resonance image. The intensity of the colour in the saturation map is proportional to the amount of signal depletion that has occurred as a result of the HyperCEST pre-pulse. The saturation map shows a strong CB6 Hyper-CEST signal depletion. The control syringe demonstrates no depletion and is indicated in the saturation map as an absent "signal".

Figure 5:
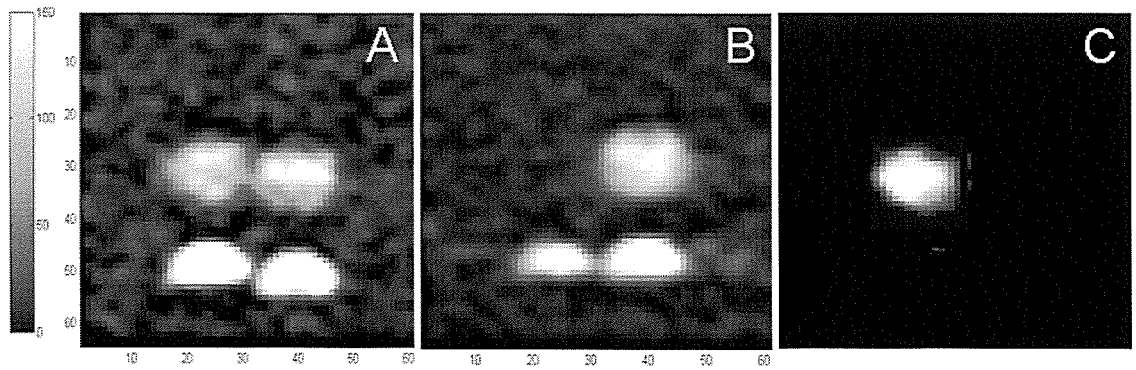
FIG. 5. A) Xenon is polarized using Spin Exchange Optical Pumping (SEOP). In SEOP, xenon flows into a chamber containing rubidium gas vapor in the presence of a magnetic field. A laser tuned to the D-transition of Rb excites the rubidium. Xe colliding with the Rb results in a spin exchange, whereby a greater proportion of Xe atoms are in the lower energy spin state (red). B) The CB6 solution is intravenously injected into the tail vein and allowed to bio-distribute. C) The rat is mechanically ventilated with a mixture of 80% xenon/20% oxygen. The rat inhales HP Xe gas which enters the vasculature via the lungs. The HP Xe interacts with the CB6 cage, diffusing in and out of the cage. D) A HyperCEST saturation pre-pulse is applied at the chemical shift frequency of the Xe-CB6 complex (124.3 ppm), depolarizing the Xe in the cage (blue). Because of exchange, this results in a reduction of signal in the dissolved reservoir. E) During imaging, an RF pulse is applied at the chemical shift of Xe-CB6, depolarizing only the Xe within the CB6 cage. As the depolarized xenon exchanges out of the CB6 cage, it reduces the pool of polarized (detectable) Xe atoms (red). The reduction of MR signal compared to a control signal indicates the presence of CB6 cages.
Figure 6:
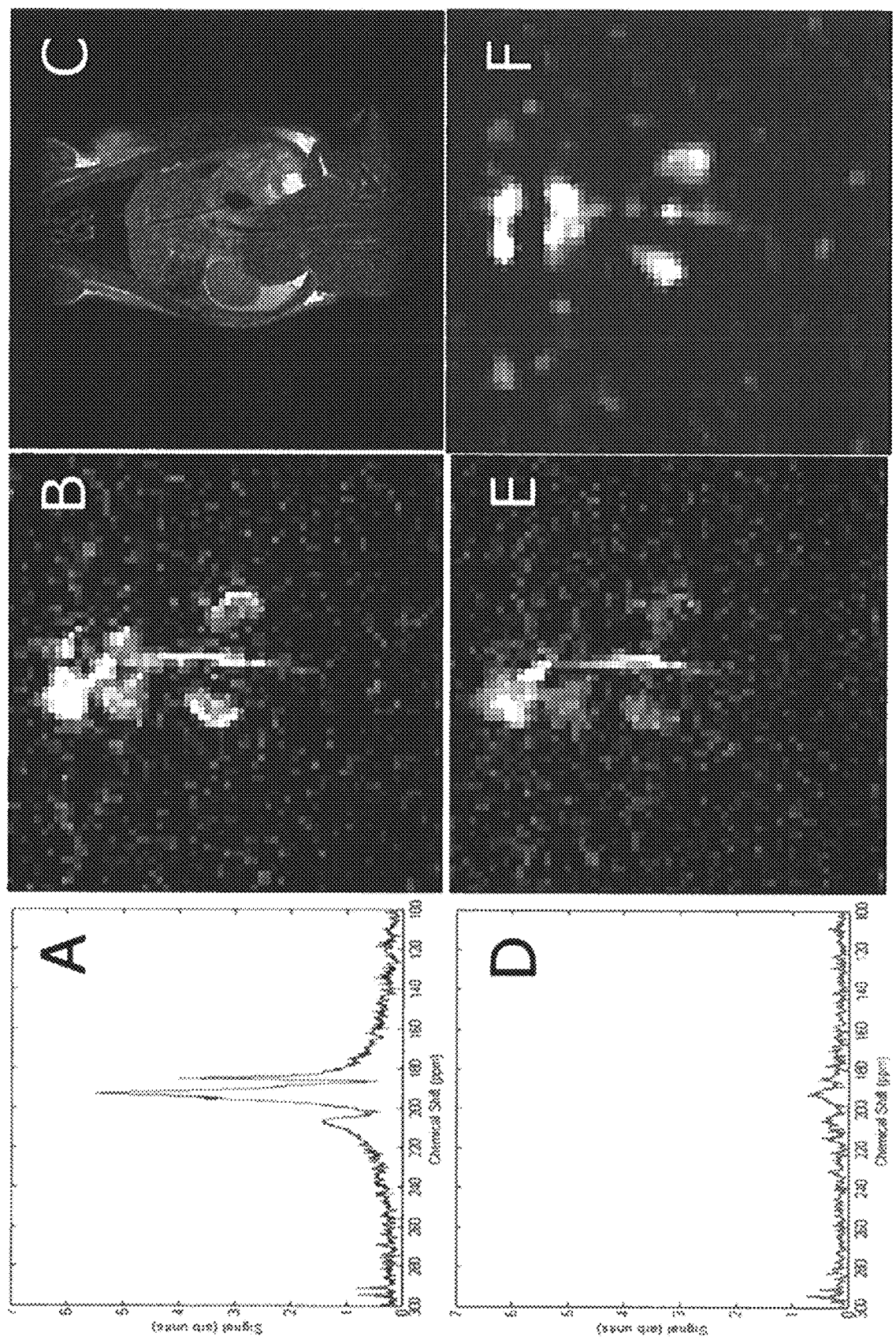
FIG. 6—MR spectra and images for the abdomen of a Sprague-Dawley rat following IV injection of 3 mL of 10 mM CB6 solution. A) Free induction decay (FID) acquired following the application of an off-resonance (control) pre-pulse at +260.3 ppm. B) FID acquired following the application of an on-resonance HyperCEST pulse at +124.3 ppm. Notice the reduction in the SNR of the primary peak indicating a HyperCEST depletion. C) A $^1$H Turbo Spin Echo MR localizer image of the abdomen. D) A 2D gradient echo (GE) Xe MR image following the application of an off-resonance pre-pulse (+260.3 ppm). E) Same as D) but following an on-resonance HyperCEST saturation pre-pulse (+124.3), which destroys the polarization of the Xe in the CB6 cage. As these depolarized Xe atoms leave the cage, they reduce the pool of polarized Xe in the blood, thereby reducing the MR signal. F) A saturation map constructed by subtracting, pixel-by-pixel, the on-resonance HyperCEST image from the off-resonance control image, and dividing by the off-resonance control image. This measures signal depletion and indicates the location of the CB6 cage molecule.
Figure 7:
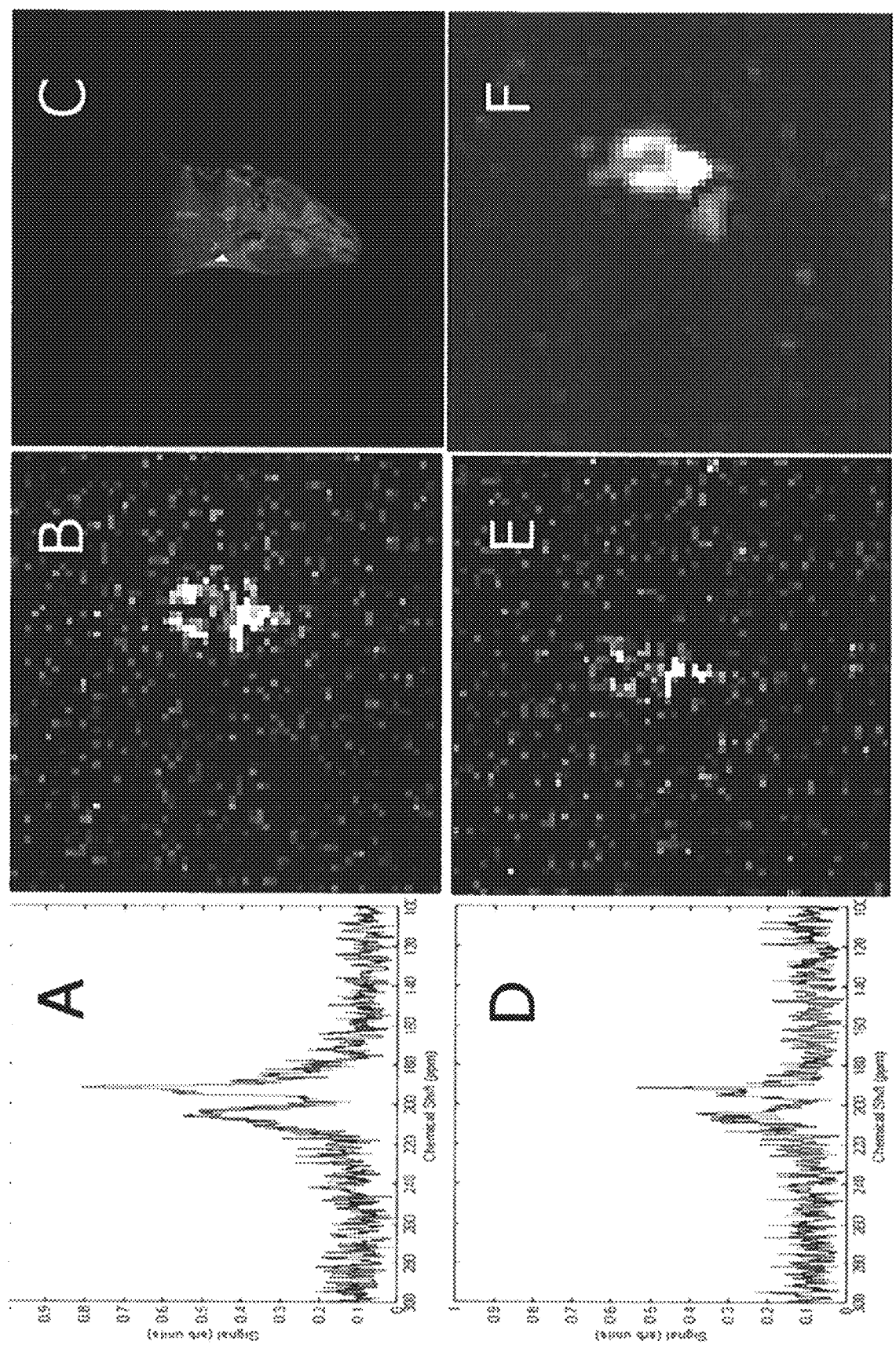
FIG. 7—MR spectra and images from the brain of a Sprague-Dawley rat following IV injection of 3 mL of 10 mM CB6 solution. Legends for all panels are identical to FIG. 6, but in the brain instead of the abdomen.

A 10 mM solution of the CB6 cage molecule dissolved in 1×PBS (pH 7.2) was prepared. 3 mL of the CB6 solution was injected into the tail vein catheter of a Sprague-Dawley rat and allowed to bio-distribute for 30 minutes. An endotracheal tube was surgically placed in the anaesthetized rat, and the rat was ventilated with 100% oxygen using a custom made ventilator. The rat was placed into a whole body custom made rat RF coil. Five seconds prior to xenon MR image acquisition, the rat was ventilated with a gas mixture of 80% xenon/20% oxygen. We acquired free induction decay (FID) magnetic resonance spectra (MRS) (FIGS. 5 & 6, A & D) from both the abdomen and head of the rat. The MR spectrum from the abdomen revealed three resolvable peaks at +184 ppm, +192.5 ppm, and +207 ppm with respect to the 29Xe gas phase chemical shift frequency (referenced to 0 ppm) (FIG. 6A). We did not observe a peak corresponding to the $^{129}$Xe-CB6 peak, as previously reported (10). We attribute this to a variety of susceptibility and line broadening effects occurring in vivo. By applying a HyperCEST pre-pulse at the known chemical shift frequency of $^{129}$Xe-CB6 (+124.3 ppm) (38), we acquired an MR spectrum with an 86% reduction in signal intensity compared to the off-resonance control spectrum (FIG. 6D). We repeated this technique after the rat was placed into a custom made rat head RF coil (FIGS. 7A & D). By applying a HyperCEST pre-pulse (+124.3 ppm), we observed a 38% reduction in signal intensity of the MR signal from the brain of the rat.

We obtained a HyperCEST depletion spectrum of CB6 within the abdomen and brain of the rat by collecting a series of FID spectra at various chemical shift frequency offsets with off- and on-resonance saturation pre-pulses. The rat was ventilated with the xenon/oxygen mixture and sequential FID spectra were acquired with off- and on-resonance saturation pre-pulses. The HyperCEST depletion spectrum indicated a maximum HyperCEST depletion at −66 ppm.

We then acquired $^1$H turbo spin echo (TSE) MR images to correlate the xenon signal with its anatomical location. Immediately prior to $^{129}$Xe image acquisition, the rat was ventilated with xenon as described above. The imaging sequence began with a saturation pre-pulse consisting of sixteen 20 ms 3-lobe sinc pulses with a 3 sec pulse interval applied at on-resonance (+215 ppm) and off-resonance (+124.3 ppm) chemical shift frequencies. $^{129}$Xe gradient echo (GE) images were acquired with both on-resonance and off-resonance saturation pre-pulses (FIGS. 6 & 7B & E). The off-resonance MR images revealed the distribution of xenon throughout the areas of the rat anatomy known to have high perfusion rates such as the brain, aorta, kidney, lungs and heart (FIGS. 6 & 7B). By applying the HyperCEST saturation pulses, we observed a reduction in signal in areas containing the CB6 molecules (FIGS. 6 & 7E).

Figure 8:
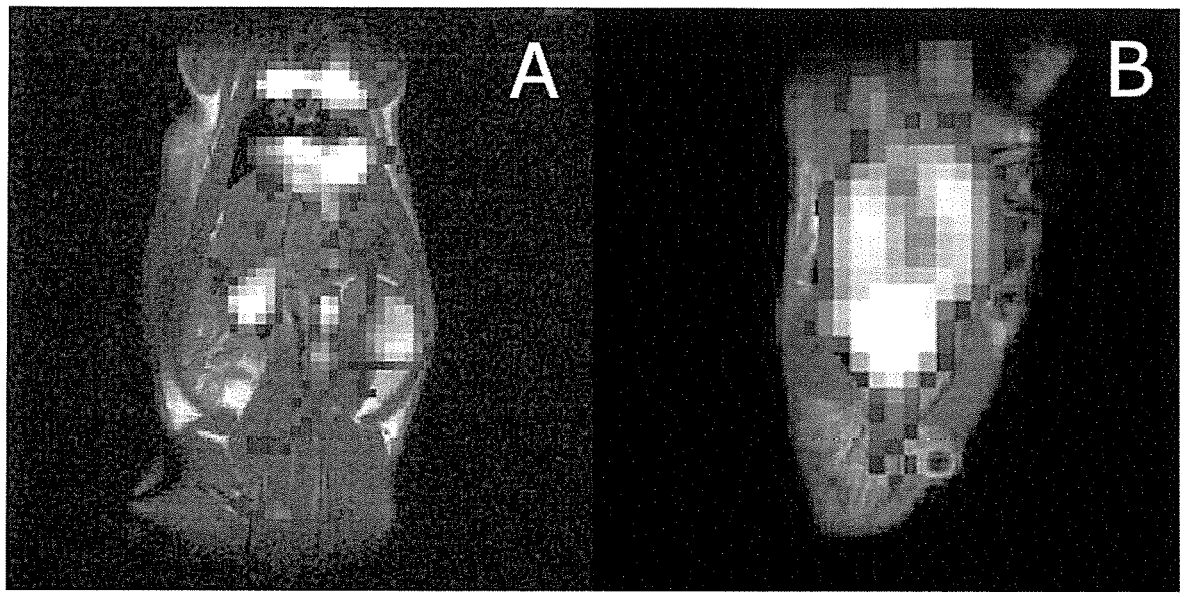
FIG. 8—A) HyperCEST saturation map of a rat abdomen overlaid on a 1H MR image showing the location of the CB6 cage contrast agent. Accumulation is noted in the heart, lungs, aorta, kidneys, and bladder. B) Same as A) but of the rat brain. A strong signal is observed in the brain, and a weaker bilateral signal is observed from either the musculature or the carotid arteries.

By subtracting the on-resonance control images from the off-resonance HyperCEST images (FIGS. 6 & 7F), and registering to the $^1$H localizer images (FIGS. 6 & 7C), we selectively imaged the areas of CB6 molecules that were localized to the brain, heart, lungs, aorta, carotid arteries, and kidneys (FIG. 8). Interestingly, we also observed a weak HyperCEST signal enhancement from the bladder of the rat (FIG. 8A). This observation supports the hypothesis that CB6 is excreted by the kidneys and ends up in the urine contained within in the bladder. We also created a Hyper-CEST saturation map in the brain of the rat (FIG. 8B).

We calculated the SAR of this pulse sequence and obtained an SAR of 0.025 W/kg which is well below the FDA SAR limit of 4 W/kg.

This work is the first report to obtain HyperCEST data from a xenon-encapsulating cage molecule in whole blood and within the vasculature of a living rat.

EXPERIMENTAL

Sample Preparation

A 2.5 mM solution of cucurbituril (CB6) was made by dissolving 50 mg of CB6 (Sigma-Aldrich, St. Louis, USA) in 10 mL of 1× phosphate buffered saline (PBS) at pH 7.2 at room temperature. The mixture was shaken gently. Ten mL of the CB6-PBS solution was mixed with 10 mL of fresh citrated bovine blood (Cederlane, Burlington Calif.) within a 30 mL syringe to create a 2.5 mM solution of CB6 in a blood solution. The control sample was prepared in an identical manner as the CB6 solution except CB6 was omitted. The control sample contained 10 mL of PBS and 10 mL of bovine blood.

Serial dilutions of CB6 in blood were made by adding an appropriate amount of blood to the 2.5 mM stock solution.
$^{129}$Xe NMR Spectra $^{129}$Xe gas was polarized to 30% using a Xemed polarizer (Xemed, Durham, N.H.). 7.5 mL of HP $^{129}$Xe gas was introduced into the syringe over 5 s from the Tedlar bag in the pressure chamber which was pressurized at 3 psi above atmosphere. The solution and gas were mixed by agitating the syringe for approximately 12 s. Approximately 3 mL of $^{129}$Xe dissolved in the blood/PBS solvent, the remaining undissolved $^{129}$Xe was ejected from the syringe, yielding an effective $^{129}$Xe concentration of 7.5 mM. The procedure was repeated for each spectral acquisition for the HyperCEST depletion spectrum. The 30 mL syringe containing the CB6-blood solution was placed inside a custom RF coil tuned to the Larmor frequency of 129Xe (35.33 MHz) at 3T. A Philips Achieva 3T clinical scanner was used to acquire all NMR spectra and MR images. A free induction decay (FID) was collected and the chemical shift of the $^{129}$Xe/CB6 complex was noted. Ref $B_1$ is a parameter of Philips MR scanners and is used to calculate the RF pulse length. The scanner uses the pulse length and flip angle to determine the amplitude of the RF pulse and field strength. For these experiments, the scanner set a B1 field strength of 1.18 µT. For the NMR spectra and images, a pulsed saturation pre-pulse train consisting of 16-6 ms 3-lobe sinc pulses with 3 ms pulse intervals was applied +124.3 ppm off resonance from the gas phase peak which corresponds to the chemical shift of the CB6-Xe complex. For initial HyperCEST depletion measurements, control spectra were collected with an off resonance saturation pre-pulse at 258 ppm. A HyperCEST depletion spectrum was collected by measuring HyperCEST depletion at various shift offsets from the CB6/Xe peak. A minimum of 3 spectra were collected at each chemical shift and the mean signal depletion was plotted as a function of the frequency of the chemical shift offset. The signal-noise ratio (SNR) of each spectrum was calculated using MATLAB (MathWorks, Natick Mass.). Signal depletion values due to the HyperCEST effect were measured by subtracting the HyperCEST saturation spectrum SNR from the control spectrum SNR and dividing by the control SNR.
Rat Preparation All animal procedures were approved by the Lakehead University Animal Care Committee. Sprague-Dawley rats (n=6) (Charles River, Sherbrook QC) weighing between 300-400 g were anesthetized using 4 LPM of isoflurane until their corneal reflex became absent. Once the rats were anaesthetized, a tail vein catheter was placed and an intravenous (IV) infusion of propofol was started (45 mg/kg/hr). A second tall vein catheter (in the second tall vein) was inserted for IV access.

A midline incision was made in the neck of the rat and the trachea localized. A 1 mm semi circumscribed incision was made in the trachea and an endotracheal catheter was inserted into the trachea. The neck was sutured closed. The endotracheal tube was connected to a custom made ventilator and the rat was placed on oxygen at 60 breaths per minute with a tidal volume of 5 mL. A Positive End Expiratory Pressure of 20 mBar was measured.

3 mL of 10 mM CB6 solution was injected over 2 minutes into the tail vein catheter.

The rats were placed inside a custom dual-tuned ($^1$H/$^{129}$Xe) Birdcage RF coil with a diameter of 80 mm.

Following data acquisition, the rats were euthanized by IV injection of pentobarbital.

Magnetic Resonance Imaging

A Philips Achieva 3T clinical scanner was used to acquire all MR spectra and MR images. $^{129}$Xe gas was polarized to 30% using a Xemed polarizer (Xemed, Durham, N.H.).

The magnetic field of the Philips Achieva 3T scanner was shimmed on the $^1$H signal using a mineral-oil phantom of approximately the same size as the rat to correct for $B_0$ inhomogeneities in order to improve the spectral resolution of the acquisitions.

T2-weighted $^1$H turbo spin echo (TSE) multi-slice images (TR=2 s, TE=1.67 ms, flip angle 12 degrees, slice thickness 2 mm) were acquired located on the intraperitoneal space of the rat with a field of view of 150 mm×150 mm and a matrix size of 256×256, yielding an in-plane resolution of 0.586 mm.

30 minutes following CB6 injection, the ventilator was set to dispense xenon to the rat. A 5 second xenon wash in period was provided, followed by the administration of an 80% xenon/20% oxygen mixture for the duration of the MR scan. Xenon 2D gradient echo images were acquired with a field of view of 150 mm×150 mm with a matrix size of 64×64 and an in-plane resolution of 2.34 mm, TR=197 ms, TE=1.67 ms, a flip angle of 40 degrees, bandwidth 300 Hz/pixel. On- and off-resonant saturation pre-pulses (+124.3 ppm & +260.3 ppm respectively) as noted above were applied as part of the acquisition pulse sequence. A wait period of 5 minutes between on- and off-resonant images was provided to ensure that all xenon gas had washed out of the blood stream. For some acquisitions, the images with off-resonant saturation pre-pulses were applied first followed by the images with on-resonant saturation pre-pulses. In other acquisitions the images with on-resonant saturation pre-pulses were applied first. We did this to account for a possible ordering effect to ensure that we were indeed measuring the depolarization of Xe because of the saturation pre-pulses and not the depolarization of xenon with time. Images were collected and analyzed using MATLAB. A convolution filter consisting of a 5×5 array that approximates a Gaussian distribution with a normalization factor to maintain signal intensity was applied. The images were thresholded to capture the entire xenon signal dissolved in the blood. Saturation maps were produced by comparing off-resonance and on-resonance $^{129}$Xe images. Background signal noise was segmented and removed for image clarity using a mask for all images.

The HyperCEST saturation maps were overlaid onto the $^1$H image using GIMP image processing software.

HyperCEST Depletion Spectra 30 minutes following injection of CB6, the ventilator was set to continuously dispense an 80% xenon/20% oxygen mixture to the rat. Following a washing period of 15 seconds, $^{129}$Xe free induction decay (FID) spectra were acquired with both off- and on-resonance saturation pre-pulses (16×20 ms, 5 ms pulse interval, 3 lobe sinc pulse) at a variety of chemical shift offsets. To eliminate the possibility of ordering effects, the off-resonance and on-resonance acquisition order were alternated. The signal to noise ratio (SNR) of each spectrum was calculated using MATLAB. The HyperCEST depletion at each chemical shift offset was calculated and plotted using Microsoft Excel.

Specific Absorption Rate Simulations

Four 1 L saline bags were placed in a $^1$H-$^{129}$Xe dual tuned head coil (Clinical MR Solutions LLC, Brookfield Wis.) to simulate a human head. 3-lobe sinc pre-saturation pulse and gradient echo acquisition pulses were applied. $P_{for}$ and $P_{rev}$ were measured and average power, $P_{avg}$, were calculated. SAR was calculated by dividing $P_{avg}$ by 4 kg, the mean weight of a human head.

The scope of the claims should not be limited by the preferred embodiments set forth in the examples but should be given the broadest interpretation consistent with the description as a whole.

REFERENCES

1. Stevens T, K, Palaniappan M, Ramirez M, Francis D, Wemmer and A, Pines HyperCEST Detection of a 129Xe-Based Contrast Agent Composed of Cryptophane-A Molecular Cages on a Bacteriophage Scaffold. Magn. Reson. Med. 2013; 69: 1245-1252.
2. Spence M, S, Rubin I, Dimitrov E, Ruiz D, Wemmer A, Pines S, Yao F, Tian and P, Schultz Functionalized xenon as a biosensor. Proc. Natl. Acad. Sci. 2001; 98: 10654-10657.
3. Walker T, and W, Happer Spin-exchange optical pumping of noble-gas nuclei. Rev. Mod. Phys. 1997; 69: 629-642.
4. Albert M, S, G, D, Cates B, Driehuys W, Happer B, Saam C, S, Springer and A, Wishnia Biological magnetic resonance imaging using laser-polarized 129Xe. Nature. 1994; 370: 199-201.
5. Schröder L, T, Lowery C, Hilty D, Wemmer and A, Pines Molecular Imaging Using a Targeted Magnetic Resonance Hyperpolarized Biosensor. Science. 2006; 314: 446-449.
6. Kunth M, C, Witte A, Hennig and L, Schroder Identification, classification, and signal amplification capabilities of high-turnover gas binding hosts in ultra-sensitive NMR. Chem. Sci. 2015.
7. Rose H, M, C, Witte F, Rossella S, Klippel C, Freund and L, Schrider Development of an antibody-based, modular biosensor for 129 Xe NMR molecular imaging of cells at nanomolar concentrations. Proc. Natl. Acad. Sci. 2014; 111: 11697-11702. DOI: 10.1073/pnas.1406797111.
8. Shapiro M, G, R, M, Ramirez L, J, Sperling G, Sun J, Sun A, Pines D, V Schaffer and V, S, Bajaj Genetically encoded reporters for hyperpolarized xenon magnetic resonance imaging. Nat. Chem. 2014; 6: 629-634. DOI: 10.1038/nchem.1934.

9. Kotera N, N, Tassali E, Léonce C, Boutin P, Berthault T, Brotin J, P, Dutasta L, Delacour T, Traoré D, A, Buisson F, Taran S, Coudert and B, Rousseau A sensitive zinc-activated 129Xe MR probe. Angew. Chemie—Int. Ed. 2012; 51: 4100-4103. DOI: 10.1002/anle.201109194.
10. Tassali N, N, Kotera Y, Boulard B, Rousseau E, Dubost T, Brotin J, Dutasta and P, Berthault Smart Detection of Toxic Metal Ions, Pb2+ and Cd2+, Using a 129Xe NMR-Based Sensor. Anal. Chem. 2014; 86: 1783-1788.
11. Chaffee K, E, H, a. Fogarty T, Brotin B, M, Goodson and J,-P, P, Dutasta Encapsulation of small gas molecules by cryptophane-111 in organic solution. 1. Size- and shape-selective complexation of simple hydrocarbons. J. Phys. Chem. A. 2009; 113: 13675-13684. DOI: 10.1021/jp903452k.
12. Mynar J, L, T, J, Lowery D, E, Wemmer A, Pines and J, M, J, Fréchet Xenon biosensor amplification via dendrimer-cage supramolecular constructs. J. Am. Chem. Soc. 2006; 128: 6334-5. DOI: 10.1021/ja061735s.
13. Bai Y, P, A, Hill and I, J, Dmochowski Utilizing a water-soluble cryptophane with fast xenon exchange rates for picomolar sensitivity NMR measurements. Anal. Chem. 2012; 84: 9935-41. DOI: 10.1021/ac302347y.
14. Wang Y, and I, Dmochowski Cucurbit[6]uril is an ultrasensitive 129Xe NMR contrast agent. Chem. Commun. 2015; 51: 8982-8985. DOI: 10.1039/C5CC01826A.
15. Schnurr M, J, Sloniec-Myszk J, Döpfert L, Schrider and A, Hennig Supramolecular Assays for Mapping Enzyme Activity by Displacement-Triggered Change in Hyperpolarized (129) Xe Magnetization Transfer NMR Spectroscopy. Angew. Chem. Int. Ed. Engl. 2015; 54: 13444-7. DOI: 10.1002/anie.201507002.
16. Stevens T, K, R, M, Ramirez and A, Pines Nanoemulsion contrast agents with sub-picomolar sensitivity for xenon NMR. J. Am. Chem. Soc. 2013; 135: 9576-9579. DOI: 10.1021/ja402885q.
17. Bal Y, Y, Wang M, Goulian A, Driks and I, J, Dmochowski Bacterial spore detection and analysis using hyperpolarized 129Xe chemical exchange saturation transfer (Hyper-CEST) NMR. Chem. Sci. 2014; 5: 3197-3203. DOI: 10.1039/b000000x/Bai.
18. Dowhos K, M, M, S, Fox I, K, Ball T, Li G, Gajawada J, Wentzell B, DeBoef and M, S, Albert Enhanced 129Xe Hyper-CEST Efficiency Using PK11195 Functionalized Cryptophane-A. Int. Soc. Magn. Reson. Med. Annu. Meet. 2014; In: International Society for Magnetic Resonance in Medicine Annual Meeting. p. 3537.
19. Wang Y, B, W, Roose J, P, Philbin J, L, Doman and I, J, Dmochowski Programming A Molecular Relay for Ultrasensitive Biodetection through 129 Xe NMR. Angew. Chemie. 2015; n/a-n/a. DOI: 10.1002/ange.201508990.
20. Riggle B, A, Y, Wang and I, J, Dmochowski A "Smart" 128Xe NMR Biosensor for 20 pH-Dependent Cell Labeling. J. Am. Chem. Soc. 2015; 137: 5542-8. DOI: 10.1021/jacs.5b01938.
21. Seward G, K, Y, Bai N, S, Khan and I, J, Dmochowski Cell-compatible, integrin-targeted cryptophane-(129)Xe NMR biosensors. Chem. Sci. 2011; 2: 1103-1110. DOI: 10.1039/C1SC00041A.
22. Bifone A, Y, Q, Song R, Seydoux R, E, Taylor B, M, Goodson T, Pietrass T, F, Budinger G, Navon and A, Pines NMR of laser-polarized xenon in human blood. Proc. Natl. Acad. Sci. U.S.A 1996; 93: 12932-12936.
23. Wolber J, A, Cherubini a S, Dzik-Jurasz M, O, Leach and A, Bifone Spin-lattice relaxation of laser-polarized xenon in human blood. Proc. Natl. Acad. Sci. U.S.A 1999; 96: 3664-3869.
24. Albert M, S, D, Balamore D, Kacher A, Venkatesh and F, Jolesz Hyperpolarized 129Xe T1 in oxygenated and deoxygenated blood. NMR Biomed. 2000; 13: 407-414.
25. Albert M, D, Kacher D, Balamore A, Venkatesh and F, Jolesz T1 of (129)Xe in blood and the role of oxygenation. J. Magn. Reson. 1999; 140: 264-273. DOI: 10.1006/jmre.1999.1836.
26. Witte C, V, Martos H, M, Rose S, Reinke S, Klippel L, Schrider and C, Hackenberger Angewandte Live-cell MRI with Xenon Hyper-CEST Biosensors Targeted to Metabolically Labeled Cell-Surface Glycans. 2015; 2806-2810. DOI: 10.1002/anie.201410573.
27. Klippel S, J, D pfert J, Jayapaul M, Kunth F, Rossella M, Schnurr C, Witte C, Freund L, Schröder J, Dopfert J, Jayapaul M, Kunth F, Rossella M, Schnurr C, Witte C, Freund and L, Schroder Cell tracking with caged xenon: Using cryptophanes as MRI reporters upon cellular internalization. Angew. Chemie—Int. Ed. 2014; 53: 493-496. DOI: 10.1002/anie.201307290.
28. Schnurr M, K, Sydow H, M, Rose M, Dathe and L, Schrider Brain Endothelial Cell Targeting Via a Peptide-Functionalized Liposomal Carrier for Xenon Hyper-CEST MRI. 2015; :40-45. DOI: 10.1002/adhm.201400224.
29. Boutin C, A, Stopin F, Lenda T, Brotin J, P, Dutasta N, Jamin A, Sanson Y, Boulard F, Leteurtre G, Huber A, Bogaert-Buchmann N, Tassali H, Desvaux M, Carrire and P, Berthault Cell uptake of a biosensor detected by hyperpolarized 129Xe NMR: The transferrin case. Bioorganic Med. Chem. 2011; 19: 4135-4143. DOI: 10.1016/j.bmc.2011.05.002.
30. Hill P, A, Q, Wei R, G, Eckenhoff and I, J, Dmochowski Thermodynamics of Xenon Binding to Cryptophane in Water and Human Plasma Thermodynamics of Xenon Binding to Cryptophane in Water and Human. Biopolymers. 2007; 9262-9263. DOI: 10.1021/ja072965p.
31. Kunth M, C, Witte and L, Schröder Continuous-wave saturation considerations for efficient xenon depolarization. NMR Biomed. 2015; 28: 601-606. DOI: 10.1002/nbm.3307.
32. Alon L, C, M, Deniz R, Brown D, K, Sodickson and Y, Zhu Method for in situ characterization of radiofrequency heating in parallel transmit MRI. Magn. Reson. Med. 2013; 69: 1457-1465.
33. Tseng C, S, Peled L, Nascimben E, Oteiza R, Walsworth and F, Jolesz NMR of laser-polarized 129Xe in blood foam. J. Magn. Reson. 1997; 126: 79-86.
34. Meldrum T, V, S, BajaJ D, E, Wemmer and A, Pines Band-selective chemical exchange saturation transfer Imaging with hyperpolarized xenon-based molecular sensors. J. Magn. Reson. 2011; 213: 14-21. DOI: 10.1016/j.jmr.2011.06.027.
35. Khan, N. S., Riggle, B. A., Seward, G. K., Bai, Y. & Dmochowski, I. J. Cryptophane-Folate Biosensor for 129 Xe NMR. *Bioconjug. Chem.* 26, 101-109 (2015).
36. Bartik, K., Luhmer, M., Dutasta, J. P., Collet, A. & Reisse, J. 129Xe and 1H NMR study of the reversible trapping of xenon by cryptophane-A in organic solution. J. Am. Chem. Soc. 120, 784-791 (1998).
37. Happer, W. Optical Pumping. Rev. Mod. Phys. 44, 169-240 (1972).
38. Hane, F. at al. HyperCEST Detection of Cucurbit[6]uril in Whole Blood Using an Ultrashort Saturation Pre-pulse Train. Contrast Media Mol. Imaging (2016).

39. Radiology, E. S. of. Medical imaging in personalised medicine: a white paper of the research committee of the European Society of Radiology (ESR). Insights Imaging 6, 141-155 (2015).

40. Keppler, J. & S, C. P. A Cost Analysis of Positron Emission Tomography. Pract. Radlol. 177, 31-40 (2001).

The invention claimed is:

1. An in vivo method of magnetic resonance imaging comprising:
    injecting a solution comprising tagged supramolecular xenon cages into a subject;
    while ventilating said subject with a mixture of oxygen gas and hyperpolarized xenon gas such that xenon in the tagged supramolecular xenon cages exchange with the hyperpolarized xenon gas, thereby forming tagged supramolecular hyperpolarized xenon cages, said tagged supramolecular hyperpolarized xenon cages having a chemical shift frequency;
    applying a first saturation pre-pulse comprising of sixteen 6 ms 3-lobe sinc pulses with 3 ms pulse intervals at the chemical shift frequency, thereby depolarizing xenon in the tagged supramolecular hyperpolarized xenon cages;
    generating an on-resonance xenon magnetic resonance image of the subject at the chemical shift frequency;
    applying a second saturation pre-pulse comprising of sixteen 6 ms 3-lobe sinc pulses with 3 ms pulse intervals at an off-resonance frequency;
    generating an off-resonance xenon magnetic resonance image of the subject at the off-resonance frequency; and
    subtracting the off-resonance xenon magnetic resonance image from the on-resonance xenon magnetic resonance image, thereby imaging the location of the tagged supramolecular xenon cages within the subject.

2. The method according to claim 1 wherein the tagged supramolecular xenon cages selected from the group consisting of: tagged cucurbituril cages, tagged calixararene cages, tagged pillarene cages, tagged rotaxane cages and tagged pseudo-rotaxane cages.

3. The method according to claim 1 wherein the tagged supramolecular cages are tagged cucurbituril xenon cages.

4. The method according to claim 3 wherein the cucurbituril is selected from the group consisting of: cucurbituril, cucurbituril, cucurbituril, cucurbituril, and cucurbituril.

5. The method according to claim 3 wherein the cucurbituril is cucurbituril (CB6).

6. The method according to claim 1 wherein the mixture of oxygen gas and hyperpolarized xenon gas is no more than 80% xenon and at least 20% oxygen.

7. The method according to claim 6 wherein the mixture of oxygen gas and hyperpolarized xenon gas is 70 to 80% xenon and 20 to 30% oxygen.

8. An in vivo method of magnetic resonance imaging comprising:
    injecting a solution comprising tagged cucurbituril xenon cages into a subject, said tagged cucurbituril xenon cages having a chemical shift frequency;
    while ventilating said subject with a mixture of oxygen gas and hyperpolarized xenon gas such that the xenon in the tagged cucurbituril xenon cages exchanges with the hyperpolarized xenon gas, thereby forming tagged cucurbituril hyperpolarized xenon cages, said tagged cucurbituril hyperpolarized xenon cages having a chemical shift frequency;
    applying a first saturation pre-pulse comprising of sixteen 6 ms 3-lobe sinc pulses with 3 ms pulse intervals at the chemical shift frequency, thereby depolarizing xenon in the tagged cucurbituril xenon cages;
    generating an on-resonance xenon magnetic resonance image of the subject at the chemical shift frequency;
    applying a second saturation pre-pulse comprising of sixteen 6 ms 3-lobe sinc pulses with 3 ms pulse intervals at an off-resonance frequency;
    generating an off-resonance xenon magnetic resonance image of the subject at the off-resonance frequency; and
    subtracting the off-resonance xenon magnetic resonance image from the on-resonance xenon magnetic resonance image, thereby imaging the location of the tagged cucurbituril xenon cages within the subject.

9. The method according to claim 8 wherein the cucurbituril is selected from the group consisting of: cucurbituril, cucurbituril, cucurbituril, cucurbituril, and cucurbituril.

10. The method according to claim 8 wherein the cucurbituril is cucurbituril (CB6).

11. The method according to claim 8 wherein the mixture of oxygen gas and hyperpolarized xenon gas is no more than 80% xenon and at least 20% oxygen.

12. The method according to claim 8 wherein the mixture of oxygen gas and hyperpolarized xenon gas is 70 to 80% xenon and 20 to 30% oxygen.

13. The method according to claim 10 wherein the chemical shift frequency is +124.3 ppm.

14. The method according to claim 10 wherein the off-resonance frequency is +215 ppm.

* * * * *